United States Patent
Kyba et al.

(10) Patent No.: US 12,221,629 B2
(45) Date of Patent: Feb. 11, 2025

(54) METHODS FOR PRODUCING FIBROADIPOGENIC PROGENITOR CELLS

(71) Applicant: REGENTS OF THE UNIVERSITY OF MINNESOTA, Minneapolis, MN (US)

(72) Inventors: Michael S. Kyba, Minneapolis, MN (US); Natalya Goloviznina, Minneapolis, MN (US); Ning Xie, Minneapolis, MN (US); Abhijit Dandapat, Lexington, MA (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 17/346,948

(22) Filed: Jun. 14, 2021

(65) Prior Publication Data

US 2021/0388321 A1     Dec. 16, 2021

Related U.S. Application Data

(60) Provisional application No. 63/039,847, filed on Jun. 16, 2020.

(51) Int. Cl.
| | | |
|---|---|---|
| *C12N 5/077* | (2010.01) | |
| *A61K 35/34* | (2015.01) | |
| *A61P 21/00* | (2006.01) | |
| *G01N 1/30* | (2006.01) | |
| *G01N 33/569* | (2006.01) | |

(52) U.S. Cl.
CPC ............ *C12N 5/0658* (2013.01); *A61K 35/34* (2013.01); *A61P 21/00* (2018.01); *C12N 5/0653* (2013.01); *C12N 5/0656* (2013.01); *G01N 1/30* (2013.01); *G01N 33/56966* (2013.01); *C12N 2501/599* (2013.01); *C12N 2506/13* (2013.01); *G01N 2001/302* (2013.01); *G01N 2333/70596* (2013.01)

(58) Field of Classification Search
CPC .. C12N 5/0658; C12N 5/0653; C12N 5/0656; C12N 2501/599; C12N 2506/13; A61K 35/34; A61P 21/00; G01N 1/30; G01N 33/56966; G01N 2001/302; G01N 2333/70596
See application file for complete search history.

(56) References Cited

U.S. PATENT DOCUMENTS

2014/0341863 A1   11/2014  Marasco et al.

FOREIGN PATENT DOCUMENTS

WO       2020020857 A1    1/2020

OTHER PUBLICATIONS

Terp et al (Anti-Human CD73 Monoclonal Antibody Inhibits Metastasis Formation in Human Breast Cancer by Inducing Clustering and Internalization of CD73 Expressed on the Surface of Cancer Cells. J Immuno, vol. 191, 2013 (Year: 2013).*
Barnhart et al (Abstract 1476: A therapeutic antibody that inhibits CD73 activity by dual mechanisms. Cancer Research, vol. 76, Jul. 2016, (Year: 2016).*
Gaspar et al (Classification of Skeletal Muscle Diseases. Chapter & In: Myopathogy: A Practical Clinico-pathological Approach to Skeletal Muscle Biopsies, Publisher Springer, ISBN 978-981-13-1461-2, Sep. 2018) (Year: 2018).*
Costela et al (iPSCs: A powerful tool for skeletal muscle tissue engineering. J Cell Mol Med, vol. 23, Apr. 2019 (Year: 2019).*
Theret et al (Evolving Roles of Muscle-Resident Fibro-Adipogenic Progenitors in Health, Regeneration, Neuromuscular Disorders, and Aging. Frontiers in Phys, vol. 12, Apr. 2021) (Year: 2021).*
Ritso et al (Emerging skeletal muscle stromal cell diversity: Functional divergence in fibro/adipogenic progenitor and mural cell populations. Exp Cell Res, vol. 410, Nov. 2021 (Year: 2021).*
Uezumi et al (Mesenchymal progenitors distinct from satellite cells contribute to ectopic fat cell formation in skeletal muscle. Nature Cell Biology, vol. 12, Feb. 2010 (Year: 2010).*
Downey et al (Prospective heterotopic ossification progenitors in adult human skeletal muscle. Bone, vol. 71, Nov. 2014 (Year: 2014).*
Uezumi et al (Cell-Surface Protein Profiling Identifies Distinctive Markers of Progenitor Cells in Human Skeletal Muscle. Stem Cell Reports, vol. 7, Aug. 2016 (Year: 2016).*
Terp et al (Anti-Human CD73 Monoclonal Antibody Inhibits Metastasis Formation in Human Breast Cancer by Inducing Clustering and Internalization of CD73 Expressed on the Surface of Cancer Cells. J Immuno, vol. 191, 2013, hereinafter Terp) (Year: 2013).*
Barnhart et al (Abstract 1476: A therapeutic antibody that inhibits CD73 activity by dual mechanisms. Cancer Research, vol. 76, Jul. 2016, hereinafter Barnhart). (Year: 2016).*
Hejbol et al (Marker Expression of Interstitial Cells in Human Skeletal Muscle: An Immunohistochemical Study. Journal of Histochemistry & Cytochemistry 2019, vol. 67(11) 825-844) (Year: 2019).*
Contreras et al (Origins, potency, and heterogeneity of skeletal muscle fibro-adipogenic progenitors—time for new definitions. Skeletal Muscle 11, 16, 2021) (Year: 2021).*
DeMicheli et al (A reference single-cell transcriptomic atlas of human skeletal muscle tissue reveals bifurcated muscle stem cell populations.) Skeletal Muscle (2020) 10:19 (Year: 2020).*
Lombardi et al (Cardiac Fibro-Adipocyte Progenitors Express Desmosome Proteins and Preferentially Differentiate to Adipocytes Upon Deletion of the Desmoplakin Gene. Circ Res. Jun. 24, 2016; 119(1): 41-54 (Year: 2016).*

(Continued)

*Primary Examiner* — Valarie E Bertoglio
*Assistant Examiner* — Matasha Dhar
(74) *Attorney, Agent, or Firm* — Viksnins Harris Padys Malen LLP

(57) ABSTRACT

The present disclosure provides methods of producing a preparation of fibroadipogenic progenitors (FAPs) from a cell mixture. In certain embodiments, the present disclosure provides a method of producing a preparation of human FAPs from a skeletal muscle biopsy sample for later use.

15 Claims, 5 Drawing Sheets
(3 of 5 Drawing Sheet(s) Filed in Color)

(56) References Cited

OTHER PUBLICATIONS

Arrighi, N, et al., "Characterization of adipocytes derived from fibro/adipogenic progenitors resident in human skeletal muscle", Cell Death and Disease 6, e1733, 10 pages (2015).
Biferali, B, et al., "Fibro-Adipogenic Progenitors Cross-Talk in Skeletal Muscle: The Social Network", Frontiers in Physiology 10, Article 1074, 10 pages (2019).
Geoghegan, J, et al., "Inhibition of CD73 AMP hydrolysis by a therapeutic antibody with a dual, non-competitive mechanism of action", MABS 8 (3), 454-467 (2016).
Goloviznina, N, et al., "Prospective isolation of human fibroadipogenic progenitors with CD73", Heliyon 6, e04503, 4 pages (2020).
Joe, A, et al., "Muscle injury activates resident fibro/adipogenic progenitors that facilitate myogenesis", Nat Cell Biol 12(2), 153-163 (2010).
Low, M, et al., "Fibro/Adipogenic Progenitors (FAPs): Isolation by FACS and Culture", Methods in Molecular Biology 1556, 179-189 (2017).
Murphy, M, et al., "Satellite cells, connective tissue fibroblasts and their interactions are crucial for muscle regeneration", Development 138(17), 3625-3637 (2011).
Wosczyna, M, et al., "Mesenchymal Stromal Cells Are Required for Regeneration and Homeostatic Maintenance of Skeletal Muscle", Cell Rep 14, 27(7), 2029-2035 (2019).

\* cited by examiner

CD73+
CD31-CD45-

CD73-
CD31-CD45-

MyoD MHC DAPI

METHODS FOR PRODUCING FIBROADIPOGENIC PROGENITOR CELLS

CROSS REFERENCE TO RELATED APPLICATION

This application claims priority to U.S. Provisional Application No. 63/039,847 filed on 16 Jun. 2020, which is incorporated by reference herein.

GOVERNMENT FUNDING

This invention was made with government support under AR055685 awarded by the National Institute of Arthritis and Musculoskeletal and Skin Diseases of the National Institutes of Health. The government has certain rights in the invention.

BACKGROUND OF THE INVENTION

Skeletal muscle contains numerous non-myogenic supportive cell types which interact with each other and with myogenic cells to maintain muscle function and enable regenerative homeostasis. Using mouse genetic models and cell surface markers, the role of cells with fat and fibroblastic differentiation potential in coordinating the regenerative response of satellite cells to injury has become appreciated in the mouse system (Joe et al., *Nat Cell Biol* 12(2), 153-163, 2010; Murphy et al., *Development*, 138(17):3625-37, 2011; Uezumi et al., *Nat Cell Biol* 12(2), 143-152, 2010; Wosczyna et al., *Cell Rep*, 14; 27(7):2029-2035, 2019). These cells are commonly referred to as FAPs (fibroadipogenic progenitors), for their ability to differentiate into fat or matrix-secretory fibroblasts, in vitro and in vivo (Joe et al., *Nat Cell Biol* 12(2), 153-163, 2010). In the murine system, FAPs have been prospectively isolated using a combination of lineage negative (CD45, CD31, and Itga7) markers together with the positive markers PDGFRα (Uezumi et al., *Nat Cell Biol* 12(2), 143-152, 2010) or CD34 and Sca1 (Joe et al., *Nat Cell Biol* 12(2), 153-163, 2010). After severe injury, such as is generated by myotoxin injection, FAP numbers increase, but return to normal within 5 days (Joe et al., *Nat Cell Biol* 12(2), 153-163, 2010).

The importance of this cell population in muscle regeneration and injury response has been a topic of intense study in the past decade. However, there are still many unknown questions about FAP biology. One important challenge is the isolation and identification of FAPs in human skeletal muscle. There is a need for efficient and robust methods of isolating FAPs to produce high quality preparation of FAPs for basic, translational research and clinical use.

SUMMARY OF THE INVENTION

Certain embodiments of the invention provide a method of producing a preparation of fibroadipogenic progenitors (FAPs), comprising:
contacting a cell mixture comprising FAPs with an anti-CD73 agent having affinity for CD73, wherein the agent has an optional tag; and
separating the anti-CD73 agent labeled cells from the cell mixture to produce the preparation of FAPs.

Certain embodiments of the invention provide a method of producing adipocytes comprising:
producing and culturing the preparation of FAPs as described herein,
wherein the culturing is under adipogenic conditions such that the FAPs differentiate into adipocytes or are committed to differentiate into adipocytes.

Certain embodiments of the invention provide a method of producing fibroblasts comprising:
producing and culturing the preparation of FAPs as described herein,
wherein the culturing is under fibrogenic conditions such that the FAPs differentiate into fibroblasts or are committed to differentiate into fibroblasts.

Certain embodiments of the invention provide a method of treating a muscle disorder in an animal in need thereof comprising:
producing a preparation of FAPs or differentiated cells derived from the FAPs using a method as described herein, and
administering an effective amount of the preparation of FAPs or differentiated cells to the animal.

Certain embodiments of the invention provide a method of testing a compound comprising:
producing and culturing a preparation of FAPs or differentiated cells derived from the FAPs using a method as described herein,
contacting a test compound with the cultured preparation of FAPs or differentiated cells, and providing an indication of the efficacy of the test compound in inhibiting fibrosis, inhibiting fat cell differentiation, or promoting muscle homeostasis, repair or myogenesis.

Certain embodiments of the invention provide a preparation of FAPs or differentiated cells derived from FAPs, which are produced by a method as described herein.

Certain embodiments of the invention provide a composition comprising the preparation of FAPs or differentiated cells and a carrier.

Certain embodiments of the invention provide a method of treating a muscle disorder in an animal in need thereof comprising administering an effective amount of the preparation of FAPs or differentiated cells as described herein to the animal.

Certain embodiments of the invention provide a preparation of FAPs or differentiated cells as described herein for use in a method of treating a muscle disorder.

Certain embodiments of the invention provide a preparation of FAPs or differentiated cells as described herein for use in medical therapy.

Certain embodiments of the invention provide a kit comprising:
a package, an anti-CD73 agent having affinity for CD73, and
instructions for producing a preparation of FAPs using a method as described herein.

Certain embodiments provide methods and intermediates disclosed herein that are useful for preparing FAPs or differentiated cells derived therefrom.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A: FACS analysis showing CD73 staining of single cells from human muscle biopsy. Left panel: Average fraction of CD73+CD45−CD31− cells in wildtype muscle is 4.5% (n=4). Right panel: Average fraction of CD73+CD45−

CD31− cells in wildtype muscle is 4.79% (n=8); FIG. 1B: CD73+ and CD73− were cultured in myogenic growth medium, staining with MyoD (upper panels); or cultured in myogenic differentiation medium, staining with MHC (lower panels); FIG. 1C: CD73+ and CD73− were cultured in adipogenic differentiation medium, then performed Oil red O staining. CD73− cells are not adipogenic. CD73+ cells were also cultured in fibrogenic differentiation medium, then stained with Sirius Red/Fast Green. The dual differentiation potential characterizes these cells as FAPs.

FIG. 3A: Freshly isolated cells express both CD73 and CD56; FIG. 3B: the CD56 population gains CD73 expression after ex vivo culture; FIG. 3C: PI control.

DETAILED DESCRIPTION

Figure 1A:
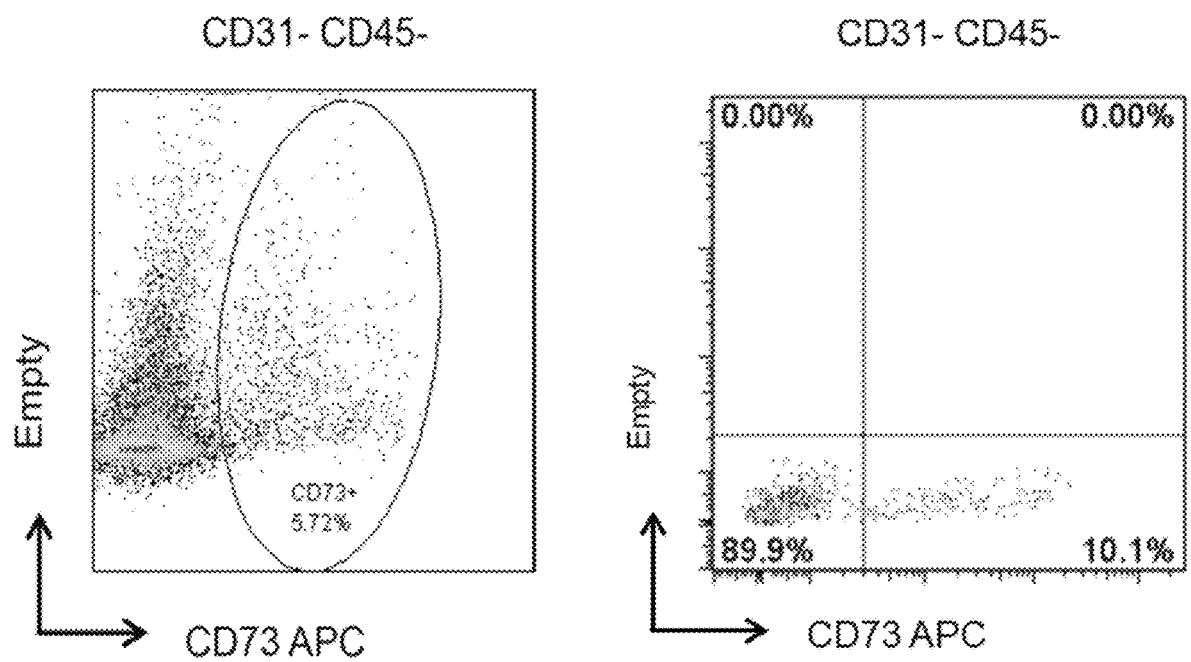
FIGS. 1A-1C. CD73 is a negative marker for human myogenic cells but a positive marker for FAPs.

FAPs (fibroadipogenic progenitors) play roles in muscle homeostasis, repair and/or myogenesis. Described herein are new and useful methods of producing a preparation of FAPs via CD73 as a selection marker. CD73, also known as ecto-5'-nucleotidase, is a cell membrane anchored enzyme that hydrolyzes AMP to adenosine, which in certain contexts may have an anti-inflammatory and/or immunosuppressive function.

As used herein, the term "fibroadipogenic progenitor" or "FAP" refers to a non-myogenic progenitor cell that is capable of differentiating into a fibroblast or adipocyte under fibrogenic or adipogenic conditions (e.g., in vitro, ex vivo, and/or in vivo). In certain embodiments, FAPs are CD73+ progenitor cells. In certain embodiments, FAPs are CD31− CD45−CD73+ progenitor cells.

Certain embodiments of the invention provide a method of producing a preparation of fibroadipogenic progenitors (FAPs), comprising:
contacting a cell mixture comprising FAPs with an anti-CD73 agent having affinity for CD73 (e.g., under conditions suitable for binding between the agent and FAP cells), wherein the agent has an optional tag; and
separating the anti-CD73 agent labeled cells from the cell mixture to produce the preparation of FAPs.

Certain embodiments of the invention provide a method of producing a preparation of fibroadipogenic progenitors (FAPs), comprising:
contacting a cell mixture comprising FAPs with an anti-CD73 agent having affinity for CD73 (e.g., under conditions suitable for binding between the agent and FAP cells), wherein the agent has an optional tag;
separating the anti-CD73 agent labeled cells from the cell mixture to produce the preparation of FAPs, and
culturing the preparation of FAPs under culturing conditions.

Certain embodiments of the invention provide a method of isolating fibroadipogenic progenitors (FAPs), comprising:
contacting a cell mixture comprising FAPs with an anti-CD73 agent having affinity for CD73 (e.g., under conditions suitable for binding between the agent and FAP cells), wherein the agent has an optional tag; and
isolating the anti-CD73 agent labeled cells from the cell mixture.

Certain embodiments of the invention provide a method of isolating fibroadipogenic progenitors (FAPs), comprising:
contacting a cell mixture comprising FAPs with an anti-CD73 agent having affinity for CD73 (e.g., under conditions suitable for binding between the agent and FAP cells), wherein the agent has an optional tag;
isolating the anti-CD73 agent labeled cells from the cell mixture, and
culturing the isolated FAPs under culturing conditions.

Certain embodiments of the invention provide a preparation of FAPs, wherein the cells are produced or isolated by a method described herein.

Certain embodiments of the invention provide a cultured clonal population of FAPs isolated or produced by a method described herein.

In certain embodiments, the methods described herein further comprise obtaining the cell mixture comprising FAPs (e.g., obtained from a biopsy or iPSCs).

Cell Mixtures and a Preparation of Progenitor Cells

In certain embodiments, the cell mixture comprising FAPs as a starting raw material is derived or dissociated from a tissue sample (e.g., heart, kidney, bone marrow or muscle). In certain embodiments, the cell mixture is derived or dissociated from a muscle sample. In certain embodiments, the muscle sample is a skeletal muscle sample. In certain embodiments, the muscle sample is a muscle biopsy sample (e.g., a fresh human muscle biopsy sample).

In certain embodiments, the cell mixture comprises skeletal muscle mononuclear cells. In certain embodiments, the cell mixture comprises lineage-negative (CD45−, CD31−) skeletal muscle mononuclear cells.

In certain embodiments, the cell mixture is derived from induced pluripotent stem cells (iPSCs).

In certain embodiments, the cell mixture comprises single cells. In certain embodiments, the cell mixture is a single cell suspension.

In certain embodiments, obtaining a cell mixture comprises mechanically reducing the size of the tissue sample (e.g., cutting or mincing), enzymatically digesting the size reduced tissue sample (e.g., incubating with collagenase) and/or separating single cells from tissue debris/cell aggregates (e.g., filtering through a cell strainer with an exemplary mesh size range of about 20 µm to about 100 µm, such as about 40 µm to about 70 µm).

In certain embodiments, the cell mixture is freshly dissociated from the tissue sample (e.g., muscle sample). As used herein, the term "dissociate" or "dissociated" refers to cells that have been separated or released from tissue (e.g., by mechanical, enzymatic, and/or chemical processes). Thus, a cell mixture that is "freshly dissociated" refers to cells recently released from tissue (e.g., having been dissociated from the tissue sample within about 24 hours, 12 hours, 6 hours, 4 hours or less). In certain embodiments, the cell mixture freshly dissociated from the tissue sample is contacted with the anti-CD73 agent shortly after dissociation. For example, in certain embodiments, the cell mixture is contacted with the anti-CD73 agent within 24, 22, 20, 18, 16, 14, 12, 10, 8, 6, 5, 4, 3, 2, 1 or 0.5 hours after dissociation from the tissue sample. In certain embodiments, the cell mixture is contacted with the anti-CD73 agent within 12, 10, 8, 6, 5, 4, 3, 2, 1 or 0.5 hours after dissociation from the tissue sample. In certain embodiments, the cell mixture is contacted with the anti-CD73 agent within 3, 2, 1 or 0.5 hours after dissociation from the tissue sample. In certain embodiments, the cell mixture is contacted with the anti- CD73 agent within 1 or 0.5 hours after dissociation from the tissue sample. In certain embodiments, the cell mixture freshly dissociated from the tissue sample is not cultured (e.g., expanded) under culturing conditions prior to contacting with the anti-CD73 agent. For example, in certain embodiments, the cell mixture freshly dissociated from the tissue sample is not cultured under adherent culturing conditions prior to contact with the anti-CD73 agent. As used herein "adherent culturing conditions" are conditions suitable for cells to adhere to the cell culture container substrate surface, which may be optionally coated (e.g., with gelatin or other protein or polymer coating that promotes cells to attach and grow). In certain embodiments, the cells of the cell mixture freshly dissociated from the tissue sample are not expanded and/or passaged under culturing conditions prior to contacting with the anti-CD73 agent.

In certain embodiments, the cell mixture is not cultured after dissociation from the tissue sample and is contacted with the anti-CD73 agent within about 4, 3, 2 or 1 hours after being dissociated.

In certain embodiments, the cell mixture freshly dissociated from the tissue sample is not trypsinized prior to contact with the anti-CD73 agent. In certain embodiments, the cell mixture freshly dissociated from the tissue sample is trypsinized prior to contact with the anti-CD73 agent.

As described in the Examples, it was determined that distinct CD73+ and CD56+ cell populations are present in fresh muscle biopsies; however, myogenic cells gain CD73 expression after being cultured ex vivo. Thus, in certain embodiments, the dissociated cell mixture is not cultured for a time period sufficient for myogenic cells to gain CD73 expression, prior to being contacted with the anti-CD73 agent. For example, in certain embodiments, a method described herein further comprises culturing the cell mixture under culturing conditions (e.g., adherent culturing conditions) for less than 7, 6, 5, 4, 3 or 2 days prior to contacting with the anti-CD73 agent. In certain embodiments, the cell mixture is cultured under culturing conditions (e.g., adherent culturing conditions) for no more than 48, 36, 24, 22, 20, 18, 16, 14, 12, 10, 8, 6, 5, 4, 3, 2, 1 or 0.5 hours prior to contacting with the anti-CD73 agent. In certain embodiments, a method described herein further comprises culturing the cell mixture under culturing conditions for no more than 6, 5, 4, 3, 2, 1 or 0.5 hours prior to contacting with the anti-CD73 agent. In certain embodiments, cultured cells are trypsinized and resuspended prior to contacting with the anti-CD73 agent.

Certain embodiments of the invention provide method of isolating, purifying or enriching FAPs from a cell mixture to produce a preparation of FAPs. In certain embodiments, CD73 is used as a single positive marker of FAPs to isolate, purify or enrich FAPs from a cell mixture. In certain embodiments, the preparation of FAPs are human FAPs. In certain embodiments, the FAPs have a surface marker phenotype of CD45− CD31− CD73+.

In certain embodiments, prior to separating CD73+ cells from the cell mixture, the fraction of CD73+ cells in the hematopoietic and endothelial lineage negative (e.g., CD45− CD31−) population of the cell mixture is about 1, 2, 3, 4, 5, 6, 7, 8, 9 or 10%. In certain embodiments, the fraction of FAPs (e.g., CD73+ cells) may account for about 4.5% or 5% of the hematopoietic/endothelial lineage negative population of the cell mixture. In certain embodiments, the fraction of FAPs account for 5±3% (e.g., 2.2%, 3.6%, 5.7%, or 6.4%) of the hematopoietic/endothelial lineage negative population of the cell mixture. In certain embodiments, the fraction of FAPs account for 5±2% of the hematopoietic/endothelial lineage negative population of the cell mixture. In certain embodiments, the fraction of FAPs account for 5±1% of the hematopoietic/endothelial lineage negative population of the cell mixture. In certain embodiments, the fraction of FAPs account for less than 11% of the hematopoietic/endothelial lineage negative population of the cell mixture. In certain embodiments, the fraction of FAPs account for less than 10% of the hematopoietic/endothelial lineage negative population of the cell mixture. In certain embodiments, the fraction of FAPs account for less than 9% of the hematopoietic/endothelial lineage negative population of the cell mixture.

In certain embodiments, prior to isolation the fraction of FAPs as described herein (e.g., CD73+ cells) account for less than 40%, 30%, 20%, 10%, 9%, 8%, or 7% of the total viable cells of the cell mixture (e.g., used as input starting population for isolating FAPs, such cell mixture may be freshly dissociated from a muscle biopsy sample and/or are not cultured in a culturing condition). In certain embodiments, the fraction of FAPs account for less than 40% of the total viable cells of the cell mixture. In certain embodiments, the fraction of FAPs account for less than 30% of the total viable cells of the cell mixture. In certain embodiments, the fraction of FAPs account for less than 20% of the total viable cells of the cell mixture. In certain embodiments, the fraction of FAPs account for less than 10% of the total viable cells of the cell mixture. In certain embodiments, the fraction of FAPs account for less than 9% of the total viable cells of the cell mixture. In certain embodiments, the fraction of FAPs account for less than 8% of the total viable cells of the cell mixture. In certain embodiments, the fraction of FAPs account for less than 7% of the total viable cells of the cell mixture.

In certain embodiments, the preparation of FAPs isolated or purified from the cell mixture has a cell purity or fraction of at least about 80, 81, 82, 83, 84, 85, 86, 87, 88, 89, 90, 91, 92, 93, 94, 95, 96, 97, 98, 99 or 100% (by cell count) of FAPs in the preparation. In certain embodiments, the preparation of FAPs has a cell purity of at least about 85% of FAPs. In certain embodiments, the preparation of FAPs has a cell purity of at least about 90% of FAPs. In certain embodiments, the preparation of FAPs has a cell purity of at least about 95% of FAPs. In certain embodiments, the preparation of FAPs has a cell purity of at least about 97% of FAPs. In certain embodiments, the preparation of FAPs has a cell purity of at least about 99% of FAPs. In certain embodiments, the preparation of FAPs has a cell purity of at least about 99.5% of FAPs. In certain embodiments, the preparation of FAPs has a cell purity of at least about 99.9% of FAPs.

In certain embodiments, the preparation of FAPs produced according to the methods described herein has a cell purity or fraction of FAPs that increases by at least 2, 3, 4, 5, 6, 7, 8, 9, 10, 11, 12, 13, 14, 15, 16, 17, 18, 19, 20, 25, 30, 35, 40, 45, 50, 60, 70, 80, 90, or 100 fold compared to the cell purity or fraction of FAPs in the cell mixture.

Anti-CD73 Agents and Tags

As used herein, the term an "anti-CD73 agent" refers to an agent that has affinity for CD73 or binds CD73 under appropriate conditions. Such an agent optionally may include a tag as described herein (e.g., an agent operably linked to a tag). In certain embodiments, the anti-CD73 agent is an antibody, fragment or derivative thereof (e.g., Fab, $Fab_2$, scFv, biscFv, diabody, triabody, tetrabody, or nanobody), an affibody, or an aptamer.

In certain embodiments, the anti-CD73 agent is a monoclonal or polyclonal antibody. In certain embodiments, the anti-CD73 agent is a mouse anti-human CD73 antibody (e.g., clone AD2, clone 7G2, clone 1D7). In certain embodiments, the anti-CD73 agent is a human anti-human CD73 antibody (e.g., TJD5). In certain embodiments, the anti-CD73 agent is a goat, rabbit, chicken, hamster or rat anti-human CD73 antibody.

In certain embodiments, the anti-CD73 agent has an optional tag. In certain embodiments, the tag is a fluorochrome (e.g., FITC, PE, APC, PE-Cy7), polypeptide tag (e.g., HIS tag, FLAG tag, GST tag, Myc tag), biotin, quantum dot or magnetic particle.

In certain embodiments, the anti-CD73 agent and the tag are directly conjugated or fused (e.g., polypeptide tag). For example, in certain embodiments, the anti-CD73 antibody is conjugated with a fluorochrome or biotin.

In certain embodiments, the tag and anti-CD73 agent is indirectly conjugated. For example, in certain embodiments, a magnetic particle coated with polysaccharide (e.g., dextran) is functionalized with an anti-CD73 antibody.

In certain embodiments, contacting the cell mixture with an anti-CD73 agent can last from about 2 minutes to about 2 hours (e.g., about 5, 10, 15, 20, 25, 30, 35, 40, 45, 50, 55, 60, 65, 70, 75, 80, 85, 90, 95, 100, 105, 110, 115 or 120 minutes). In certain embodiments, contacting the cell mixture with anti-CD73 agent can last from about 20 minutes to about 1 hour (e.g., 30 to 40 minutes).

In certain embodiments, contacting the cell mixture with anti-CD73 agent can be performed at about 0, 1, 2, 3, 4, 5, 6, 7 or 8° C.

In certain embodiments, contacting the cell mixture with anti-CD73 agent can be preceded by contacting the cell mixture with a buffer comprising a recombinant Fc protein to block non-specific binding of antibodies to Fc receptors on cell surfaces (e.g., tissue resident macrophages, dendritic cells, myeloid cells, or lymphocytes).

In certain embodiments, the anti-CD73 agent reduces CD73 enzymatic activity upon binding. In certain embodiments, the anti-CD73 agent does not reduce CD73 enzymatic activity upon binding.

In certain embodiments, the anti-CD73 agent induces CD73 cellular internalization and reduces the CD73 cell surface expression levels (e.g., under culturing condition). In certain embodiments, the anti-CD73 agent does not induce CD73 cellular internalization and does not reduce CD73 cell surface expression levels (e.g., under culturing condition).

In certain embodiments, the preparation of anti-CD73 agent labeled FAPs has reduced CD73 cell surface expression levels, increased CD73 internalization levels and/or reduced CD73 enzymatic activity levels.

In certain embodiments, the preparation of anti-CD73 agent labeled FAPs has increased intracellular levels of the anti-CD73 agent and/or its tag (e.g., under culturing condition). In certain embodiments, the preparation of anti-CD73 agent labeled FAPs has increased intracellular tag levels (e.g., fluorochrome, biotin or magnetic particle level).

In certain embodiments, the method described herein further comprises removing or releasing the anti-CD73 agent or its tag from the labeled FAPs cell surface after separating from the cell mixture. Accordingly, the preparation of anti-CD73 agent labeled FAPs become label-free or tag-free and does not have increased intracellular tag levels (e.g., fluorochrome, biotin or magnetic particle level, under culturing condition).

Secondary Agents

In certain embodiments, the method further comprises contacting the anti-CD73 agent labeled FAPs with a secondary agent, wherein the secondary agent has affinity for the anti-CD73 agent or its optional tag thereof. For example, after contacting the cell mixture with an anti-CD73 agent, the anti-CD73 agent labeled FAPs are contacted with the secondary agent.

In certain embodiments, the secondary agent is antiisotype antibody (e.g., anti-IgG1 antibody, anti-IgG2 antibody, anti-IgG (H+L) antibody, anti-Ig kappa or lambda light chain antibody).

In certain embodiments, the secondary agent is an anti-tag antibody (e.g., anti-FITC, anti-PE, anti-His tag, anti-FLAG tag, anti-GST tag, anti-Myc tag, anti-biotin antibody).

In certain embodiments, the secondary agent has a tag (e.g., fluorochrome or magnetic particle). In certain embodiments, the secondary agent is a streptavidin conjugated magnetic particle or an antibody conjugated magnetic particle.

In certain embodiments, a method described herein further comprises separating the cells labeled with the secondary agent from the cell mixture to produce the preparation of FAPs.

Co-Staining Agents

In certain embodiments, the method described herein further comprises contacting the cell mixture with co-staining agent(s) having affinity for additional marker(s) of FAPs or non-FAPs (e.g., one or more co-staining agent(s)). In certain embodiments, the co-staining agent(s) include positive selection marker(s) of FAPs (e.g., one or more), negative selection marker(s) of non-FAPs (e.g., one or more), or any combination thereof.

As described herein, additional positive selection markers may be used to further isolate FAP cells from the cell mixture, whereas negative selection markers may be used to remove or exclude non-FAP cells from the desired FAP cell preparation. Thus, cells that express a positive selection marker are retained and cells that express a negative selection marker are excluded or discarded.

The co-staining agent(s) can be incubated with the cell mixture concurrently, prior to or subsequent to contacting the cell mixture with the anti-CD73 agent.

In certain embodiments, one, two, three, four, five, six, seven, eight, nine, ten or more co-staining agents are used. In certain embodiments, two, three, four, five or six co-staining agents are used. In certain embodiments, two co-staining agents are used. In certain embodiments, three co-staining agents are used. In certain embodiments, four co-staining agents are used.

In certain embodiments, the method described herein further comprises contacting the cell mixture with a negative selection co-staining agent(s) that has affinity for a marker of non-FAP cells (e.g., endothelial lineage cell, hematopoietic lineage cell, myoblast, myocyte or satellite cell). In certain embodiments, the negative selection co-staining agent(s) has affinity for marker(s) of endothelial lineage cell, hematopoietic lineage cell, or satellite cell. For example, the negative selection co-staining agents have affinity for markers of endothelial lineage cell and hematopoietic lineage cell.

In certain embodiments, the method further comprises contacting the cell mixture with a negative selection agent(s) and separating the negative selection agent(s) labeled cells from the cell mixture.

In certain embodiments, a negative selection co-staining agent has affinity for endothelial lineage marker CD31. In certain embodiments, a negative selection co-staining agent has affinity for hematopoietic lineage marker CD45. In certain embodiments, a negative selection co-staining agent has affinity for Itga7. In certain embodiments, negative selection co-staining agents comprise an anti-CD31 agent and an anti-CD45 agent. In certain embodiments, the isolated FAPs have a phenotype of CD31−, CD45− and CD73+.

In certain embodiments, the anti-CD73 agent has a tag (e.g., fluorochrome) that is different from the tag (e.g., fluorochrome) of a negative selection co-staining agent(s). For example, the anti-CD73 agent has a fluorochrome (e.g., APC) that is different from the fluorochrome (e.g., PE-Cy7) of a negative selection co-staining agent (e.g., anti-CD31 agent and/or anti-CD45 agent).

In certain embodiments, a negative selection co-staining agent(s) that has affinity for a satellite cell marker(s) is selected from the group consisting of CD9, CD46, CD81, CD83, CD97, FGFR4, TGFBR3 and CXCR4.

In certain embodiments, the methods described herein do not comprise contacting the cell mixture with a negative selection co-staining agent(s) that has affinity for a satellite cell marker(s) selected from the group consisting of CD9, CD46, CD81, CD83, CD97, FGFR4, TGFBR3 and CXCR4.

In certain embodiments, the methods described herein comprise contacting the cell mixture with negative selection co-staining agent(s) that has affinity for CD31, CD45, CD9, CD46, CD81, CD83, CD97, FGFR4, TGFBR3, and/or CXCR4.

In certain embodiments, the methods described herein comprise contacting the cell mixture with a negative selection co-staining agent(s) that has affinity for a satellite cell marker(s) selected from the group consisting of CD9, CD46, CD81, CD83, CD97, FGFR4, TGFBR3 and CXCR4. In certain embodiments, a negative selection co-staining agent(s) that has affinity for a satellite cell marker(s) is selected from the group consisting of CD56, CD9, CD46, CD81, CD83, CD97, FGFR4, TGFBR3, CXCR4, CD82, or CD318.

In certain embodiments, the cell mixture is contacted with only a single positive selection agent (i.e., CD73). In certain embodiments, the cell mixture is not contacted with an additional positive selection agent.

In certain embodiments, the cell mixture is contacted with one or more additional positive selection co-staining agents that have affinity for additional marker(s) of FAPs. For example, a positive selection co-staining agent having affinity for additional FAPs marker(s) is selected from the group consisting of PDGFRα, CD201 and CD15. In certain embodiments, a positive selection co-staining agent is an anti-PDGFRα agent. In certain embodiments, a positive selection co-staining agent is an anti-CD201 agent. In certain embodiments, a positive selection co-staining agent is an anti-CD15 agent.

In certain embodiments, a cocktail panel comprising one or more co-staining agent(s) is selected from the group consisting of PDGFRα, CD201, CD15, CD105, CD31, CD34, CD45, Itga7, CD56, CD9, CD46, CD81, CD83, CD97, FGFR4, TGFBR3, CXCR4, CD82, CD318, CD133, CD44 and CD90.

In certain embodiments, the preparation of cells described herein comprises cells with a phenotype of CD73+ and any combination of one or more additional positive selection marker(s) (e.g., as described herein) and/or one or more negative selection marker(s) (e.g., as described herein). In certain embodiments, the method described herein further comprises contacting the cell mixture with a cocktail of co-staining agent(s) having affinity for any combination of one or more positive selection marker(s) (e.g., as described herein) and/or one or more negative selection marker(s) (e.g., as described herein).

In certain embodiments, the preparation of FAPs comprises CD73+CD201+ cells. In certain embodiments, the preparation of FAPs comprises CD73+CD201− cells. In certain embodiments, the preparation of FAPs comprises CD73+CD201+ cells and CD73+CD201− cells. In certain embodiments, the methods described herein do not comprise contacting the cell mixture with an anti-CD201 agent. In certain embodiments, the methods described herein comprise contacting the cell mixture with an anti-CD201 agent.

In certain embodiments, the preparation of FAPs comprises CD73+CD105+ cells. In certain embodiments, the preparation of FAPs comprises CD73+CD105− cells. In certain embodiments, the preparation of FAPs comprises CD73+CD105+ cells and CD73+CD105− cells. In certain embodiments, the methods described herein do not comprise contacting the cell mixture with an anti-CD105 agent. In certain embodiments, the methods described herein comprise contacting the cell mixture with an anti-CD105 agent.

In certain embodiments, the preparation of FAPs comprises CD73+CD90+ cells. In certain embodiments, the preparation of FAPs comprises CD73+CD90− cells. In certain embodiments, the preparation of FAPs comprises CD73+CD90+ cells and CD73+CD90− cells. In certain embodiments, the methods described herein do not comprise contacting the cell mixture with an anti-CD90 agent. In certain embodiments, the methods described herein comprise contacting the cell mixture with an anti-CD90 agent.

In certain embodiments, the preparation of FAPs comprises CD73+CD133+ cells. In certain embodiments, the preparation of FAPs comprises CD73+CD133− cells. In certain embodiments, the preparation of FAPs comprises CD73+CD133+ cells and CD73+CD133− cells. In certain embodiments, the methods described herein do not comprise contacting the cell mixture with an anti-CD133 agent. In certain embodiments, the methods described herein comprise contacting the cell mixture with an anti-CD133 agent.

In certain embodiments, the preparation of FAPs comprises CD73+CD34+ cells. In certain embodiments, the preparation of FAPs comprises CD73+CD34− cells. In certain embodiments, the preparation of FAPs comprises CD73+CD34+ cells and CD73+CD34− cells. In certain embodiments, the methods described herein do not comprise contacting the cell mixture with an anti-CD34 agent. In certain embodiments, the methods described herein comprise contacting the cell mixture with an anti-CD34 agent.

In certain embodiments, the preparation of FAPs comprises CD73+CD44+ cells. In certain embodiments, the preparation of FAPs comprises CD73+CD44− cells. In certain embodiments, the preparation of FAPs comprises CD73+CD44+ cells and CD73+CD44− cells. In certain embodiments, the methods described herein do not comprise contacting the cell mixture with an anti-CD44 agent. In certain embodiments, the methods described herein comprise contacting the cell mixture with an anti-CD44 agent.

In certain embodiments, the cell mixture is not contacted with a co-staining selection agent(s) having affinity for CD105 and/or CD90. For example, the cell mixture is not contacted with anti-CD105 agent (e.g., as a positive co-staining agent) and/or anti-CD90 agent (e.g., as a negative co-staining agent). In certain embodiments, the method described herein does not comprise contacting the cell mixture with anti-CD90 and anti-CD105 agents. In certain embodiments, the preparation of FAPs comprises CD73+CD105−CD90+ cells. In certain embodiments, the preparation of FAPs comprises CD73+CD105+CD90+ cells. In certain embodiments, the preparation of FAPs comprises CD73+CD105−CD90− cells. In certain embodiments, the preparation of FAPs comprises CD73+CD105+CD90− cells.

In certain embodiments, the method described herein comprises contacting the cell mixture with anti-CD90 and anti-CD105 agents.

In certain embodiments, the method described herein does not comprise contacting the cell mixture with anti-CD34, anti-CD133 and/or anti-CD44 agents. In certain embodiments, the method described herein comprises contacting the cell mixture with anti-CD34, anti-CD133 and/or anti-CD44 agents.

Separation Through Cell Sorting

In certain embodiments, separating labeled cells comprises conducting fluorescence-activated cell sorting (FACS) and/or magnetic-activated cell sorting (MACS) to separate cells. Separating anti-CD73 agent labeled cells, positive selection co-staining agent(s) labeled cells, or negative selection co-staining agent(s) labeled cells from the cell mixture may be conducted in the same step, or in separate steps.

In certain embodiments, separating labeled cells comprises conducting fluorescence-activated cell sorting (FACS) to produce the preparation of cells (e.g., via multi-color flow cytometry). In certain embodiments, FACS is conducted after contacting the cell mixture with anti-CD73 agent and/or a cocktail comprising co-staining agent(s).

In certain embodiments, separating negative selection agent labeled cells comprises conducting FACS to exclude non-FAP cells (e.g., endothelial lineage cell, hematopoietic lineage cell and/or satellite cells). For example, CD31+ and/or CD45+ cells are excluded in the flow cytometry gating step and not collected into the desired preparation of cells. In certain embodiments, CD9, CD46, CD81, CD83, CD97, FGFR4, TGFBR3 and/or CXCR4 positive cells are excluded in the flow cytometry gating step and not collected into the desired preparation of cells.

In certain embodiments, separating labeled cells comprises conducting magnetic-activated cell sorting (MACS) to produce the preparation of cells (e.g., via magnetic particles, magnetic column and/or magnetic field). For example, magnetically labeled cells can be retained in a magnetic field, while unlabeled cells flow through, resulting in separation.

In certain embodiments, separating labeled cells comprises conducting MACS (e.g., depletion MACS and/or positive selection MACS) once, twice, trice, four or five times to produce the preparation of cells. Depletion MACS steps can be repeated to increase depletion completeness of non-FAPs. Similarly, positive selection MACS steps can be repeated to increase the cell purity of FAPs in the desired preparation of cells.

In certain embodiments, in a depletion MACS step, non-FAP cells are contacted with negative selection magnetic co-staining agent(s). The remainder of the cell mixture can be collected in the flow-through fraction and is then contacted with anti-CD73 agent and/or positive selection magnetic co-staining agent(s) for a positive selection MACS step to produce the desired preparation of cells.

In certain embodiments, separating labeled cells comprises conducting FACS and MACS in tandem to produce the preparation of FAPs. For example, certain non-FAP cells (e.g., endothelial lineage cell, hematopoietic lineage cell and/or satellite cells) are depleted from the cell mixture via a depletion MACS step, then the remainder of the cell mixture in the flow-through fraction can be stained with an anti-CD73 antibody with a fluorochrome for FACS to produce the preparation of FAPs.

In certain embodiments, the separating of the negative selection co-staining agent labeled cells comprises conducting FACS and/or MACS to exclude non-FAP cells from the preparation of FAPs.

In certain embodiments, the preparation of cells comprising FAPs are produced in an untouched manner without contacting the cell mixture with an anti-CD73 agent. For example, depleting non-FAPs (e.g., myogenic progenitor cells or other lineage cells) from a cell mixture will produce a preparation of cells with a higher cell purity of FAPs compared to that of the starting cell mixture.

Cell Expansion, Differentiation, Compositions and Methods

In certain embodiments, the preparation of FAPs produced according to methods described herein are subsequently cultured for about 1 to 30 days or more (e.g., 2 to 20 days, 3 to 15 days, 4 to 10 days, 5 to 8 days) to expand and/or to differentiate the cells for later use.

In certain embodiments, the preparation of FAPs are cultured under conditions sufficient to produce a preparation of differentiated cells derived from the FAPs.

In certain embodiments, the preparation of FAPs are cultured under conditions sufficient to produce a preparation of adipocytes.

Accordingly, certain embodiments of the invention provide a method of producing adipocytes comprising:
producing the preparation of FAPs according to a method described herein, and
culturing the preparation of FAPs under adipogenic conditions (e.g., in the presence of insulin, dexamethasone and/or IBMX (3-isobutyl-1-methylxanthine)), wherein the FAPs differentiate into adipocytes and/or are committed to differentiate into adipocytes.

In certain embodiments, the preparation of FAPs is cultured under conditions sufficient to produce a preparation of fibroblasts.

Accordingly, certain embodiments of the invention also provide a method of producing fibroblasts comprising:
producing the preparation of FAPs according to a method described herein, and
culturing the preparation of FAPs under fibrogenic conditions (e.g., in the presence of TGFβ), wherein the FAPs differentiate into fibroblasts and/or are committed to differentiate into fibroblasts.

Certain embodiments also provide an adipocyte or a fibroblast produced using a method as described herein.

Certain embodiments of the invention provide a method of expanding a preparation of FAPs comprising:
producing the preparation of FAPs according to a method described herein, and
culturing the preparation of FAPs under proliferative and/or non-differentiating conditions (e.g., in the presence of fetal bovine serum and/or bFGF).

Certain embodiments of the invention provide method of testing a compound comprising:
producing and culturing a preparation of FAPs according to a method described herein,
contacting a test compound with the cultured preparation of FAPs or differentiated cells derived therefrom, and
providing/obtaining an indication of toxicity, or efficacy of the test compound in inhibiting fibrosis, inhibiting fat cell differentiation, or promoting muscle homeostasis, repair or myogenesis.

Certain embodiments provide a preparation of FAPs or differentiated cells derived from FAPs (e.g., an adipocyte or fibroblast), which are produced by a method as described herein.

Certain embodiments provide a composition comprising the preparation of FAPs or differentiated cells derived from FAPs, which are produced by a method as described herein, and a carrier. In certain embodiments, the composition is a pharmaceutical composition comprising a pharmaceutically acceptable carrier.

Certain embodiments provide a preparation of FAPs or differentiated cells as described herein for use in a method of treating a muscle disorder.

Certain embodiments provide a preparation of FAPs or differentiated cells as described herein for the use of preparing a medicament for treatment of a muscle disorder.

Certain embodiments provide a preparation of FAPs or differentiated cells as described herein for use in medical therapy.

Kit

Certain embodiments of the invention provide a kit comprising: a package, an anti-CD73 agent having affinity for CD73, and instructions for producing a preparation of FAPs using a method described herein.

In certain embodiments, the kit is a FACS kit.

In certain embodiments, the kit is a MACS kit.

In certain embodiments, the kit comprises a FAPs isolation cocktail comprising an anti-CD73 agent and optionally one or more positive selection co-staining agent(s) as described herein.

In certain embodiments, the kit further comprises a non-FAPs depletion cocktail comprising one or more negative selection co-staining agent(s) as described herein.

In certain embodiments, the kit comprises a non-FAPs depletion cocktail and a FAPs isolation cocktail.

In certain embodiments, the kit comprises an anti-CD73 antibody, an anti-CD31 antibody and an anti-CD45 antibody.

In certain embodiments, the kit comprises anti-CD73 antibody functionalized magnetic particles. In certain embodiments, the kit comprises an anti-CD73 antibody with a biotin tag and a secondary agent (e.g., streptavidin conjugated magnetic particles).

In certain embodiments, the kit further comprises a skeletal muscle dissociation kit comprising collagenase.

Certain Methods of Treatment and Muscle Disorders

FAPs prepared by a method described herein may be used to treat a number of different muscle disorders. For example, a FAPs preparation may be used to treat a muscle disorder described below.

Accordingly, certain embodiments of the invention provide a method of treating a muscle disorder in an animal in need thereof comprising:
producing a preparation of FAPs according to a method described herein,
optionally culturing the preparation of FAPs to expand and/or differentiate the FAPs, and administering an effective amount of the preparation of FAPs or differentiated cells to the animal.

Certain embodiments of the invention provide method of treating a muscle disorder in an animal in need thereof comprising:
producing a preparation of FAPs according to method described herein,
optionally culturing the preparation of FAPs under proliferative, fibrogenic or adipogenic conditions, wherein the FAPs are expanded, or differentiated into or committed to differentiate into fibroblasts or adipocytes, and
administering an effective amount of the preparation of FAPs or differentiated cells to the animal.

In certain embodiments, the animal is a mammal (e.g., human). In certain embodiments, the muscle disorder is muscular dystrophy.

In certain embodiments, the preparation of FAPs or cultured FAPs are co-administered along with a preparation of other non-FAP progenitor cells (e.g., myogenic progenitor cells) in a method described herein.

In certain embodiments, exosomes can be derived from the preparation of FAPs for use in a method of treating a muscle disorder.

In certain embodiments, a method further comprises administering at least one additional therapeutic agent or biologically active agent.

In certain embodiments, the muscle disorder is a disease, disorder or condition described below.

Causes of muscle disorders include injury or overuse, such as sprains or strains, cramps or tendinitis; a genetic disorder, such as muscular dystrophy, cancer, inflammation, such as myositis, diseases of nerves that affect muscles, infections and certain medicines.

Myopathy is a muscular disease in which the muscle fibers do not function for any one of many reasons, resulting in muscular weakness. "Myopathy" simply means muscle disease. This meaning implies that the primary defect is within the muscle, as opposed to the nerves ("neuropathies" or "neurogenic" disorders) or elsewhere (e.g., the brain etc.). Muscle cramps, stiffness, and spasm can also be associated with myopathy.

Muscular disease can be classified as neuromuscular or musculoskeletal in nature. Some conditions, such as myositis, can be considered both neuromuscular and musculoskeletal. Myopathies (also known as muscular dystrophy) in systemic disease results from several different disease processes including hereditary (presenting birth), endocrine, inflammatory (inflammatory myopathies caused by, for example, dermatomyositis, polymyositis; inclusion body myositis, viral (HIV)), paraneoplastic, infectious, drug- and toxin-induced (e.g., alcohol, corticosteroids, narcotics, colchicines, chloroquine), critical illness myopathy, metabolic, paraneoplastic myopathy, collagen related, and myopathies with other systemic disorders. Patients with systemic myopathies often present acutely or sub acutely. On the other hand, familial myopathies or dystrophies generally present in a chronic fashion with exceptions of metabolic myopathies where symptoms on occasion can be precipitated acutely. Most of the inflammatory myopathies can have a chance association with malignant lesions; the incidence appears to be specifically increased in patients with dermatomyositis.

There are many types of myopathy:

Inherited forms include: dystrophies ((or muscular dystrophies) are a subgroup of myopathies characterized by muscle degeneration and regeneration. Clinically, muscular dystrophies are typically progressive, because the muscles' ability to regenerate is eventually lost, leading to progressive weakness, often leading to use of a wheelchair, and eventually death, usually related to respiratory weakness), myotonia, neuromyotonia, congenital myopathies (which do not show evidence for either a progressive dystrophic process (i.e., muscle death) or inflammation, but instead characteristic microscopic changes are seen in association with reduced contractile ability of the muscles. Congenital myopathies include, but are not limited to: nemaline myopathy (characterized by presence of "nemaline rods" in the muscle), multi/minicore myopathy (characterized by multiple small "cores" or areas of disruption in the muscle fibers), centronuclear myopathy (or myotubular myopathy)

(in which the nuclei are abnormally found in the center of the muscle fibers), a rare muscle wasting disorder), mitochondrial myopathies (which are due to defects in mitochondria, which provide a source of energy for muscle), familial periodic paralysis, inflammatory myopathies (which are caused by problems with the immune system attacking components of the muscle, leading to signs of inflammation in the muscle), metabolic myopathies (which result from defects in biochemical metabolism that primarily affect muscle), glycogen storage diseases (which may affect muscle) and/or lipid storage disorder.

Acquired forms include: external substance induced myopathy, Drug-induced myopathy, Glucocorticoid myopathy (is caused by this class of steroids increasing the breakdown of the muscle proteins leading to muscle atrophy), Alcoholic myopathy. Myopathy due to other toxic agents, dermatomyositis produces muscle weakness and skin changes; polymyositis produces muscle weakness, inclusion body myositis (is a slowly progressive disease that produces weakness of hand grip and straightening of the knees), Myositis ossificans, Rhabdomyolysis and/or myoglobinurias.

Administration

The cells prepared as described herein can be administered to a subject by a variety of methods available to the art, including but not limited to localized injection, catheter administration, systemic injection, intraperitoneal injection, parenteral administration, intra-arterial injection, intravenous injection, intraventricular infusion, intraplacental injection, intrauterine injection, surgical intramyocardial injection, transendocardial injection, transvascular injection, intracoronary injection, transvascular injection, intramuscular injection, surgical injection into a tissue of interest or via direct application to tissue surfaces (e.g., during surgery or on a wound).

Intravenous injection is the simplest method of cell administration; however a greater degree of dependence on homing of the stem cells is required for them to reach the tissue of interest. "Homing" of the cells to the injured tissues would concentrate the implanted cells in an environment favorable to their growth and function. Pre-treatment of a patient with cytokine(s) to promote homing is another alternative contemplated in the methods of the present invention. Where homing signals may be less intense, injection of the cells directly into the muscle can produce a more favorable outcome. Certain cytokines (e.g., cellular factors that induce or enhance cellular movement, such as homing of stem cells, progenitor cells or differentiated cells) can enhance the migration of cells or their differentiated counterparts to the site of damaged muscle tissue. Cytokines include, but are not limited to, stromal cell derived factor-1 (SDF-1), stem cell factor (SCF) and granulocyte-colony stimulating factor (G-CSF). Cytokines also include any which promote the expression of endothelial adhesion molecules, such as ICAMs, VCAMs, and others, which facilitate the homing process.

Viability of newly forming tissues can be enhanced by angiogenesis. Factors promoting angiogenesis include but are not limited to VEGF, aFGF, angiogenin, angiotensin-1 and -2, betacellulin, bFGF, Factor X and Xa, HB-EGF, PDGF, angiomodulin, angiotropin, angiopoetin-1, prostaglandin E1 and E2, steroids, heparin, 1-butyryl-glycerol, nicotinic amide.

Factors that decrease apoptosis can also promote the formation of new tissue, such as muscle. Factors that decrease apoptosis include but are not limited to β-blockers, angiotensin-converting enzyme inhibitors (ACE inhibitors), AKT, HIF, carvedilol, angiotensin II type 1 receptor antagonists, caspase inhibitors, cariporide, and eniporide.

Exogenous factors (e.g., cytokines, differentiation factors (e.g., cellular factors, such as growth factors or angiogenic factors that induce lineage commitment), angiogenesis factors and anti-apoptosis factors) can be administered prior to, after or concomitantly with FAP cells. Doses for administration(s) are variable and may include an initial administration followed by subsequent administrations.

In current human studies of autologous mononuclear bone marrow cells, empirical doses ranging from 1 to $4 \times 10^7$ cells have been used. However, different scenarios may require optimization of the amount of cells injected into a tissue of interest. Thus, the quantity of cells to be administered will vary for the subject being treated. In one embodiment, between $10^4$ to $10^8$, more preferably $10^5$ to $10^7$, and most preferably, $3 \times 10^7$ stem cells or progenitor cells and optionally, 50 to 500 µg/kg per day of a cytokine can be administered to a human subject. For local muscle placement/injection, as few as 40,000 cells can be administered. However, the precise determination of what would be considered an effective dose may be based on factors individual to each patient, including their size, age, disease or injury, size damage, amount of time since the damage occurred and factors associated with the mode of delivery (direct injection—lower doses, intravenous—higher doses).

The skilled artisan can readily determine the amount of cells and optional additives, vehicles, and/or carrier in compositions and to be administered in methods of the invention. Typically, any additives (in addition to the active cell(s) and/or cytokine(s)) are present in an amount of 0.001 to 50 wt % solution in phosphate buffered saline, and the active ingredient is present in the order of micrograms to milligrams, such as about 0.0001 to about 5 wt %, including about 0.0001 to about 1 wt %, including about 0.0001 to about 0.05 wt % or about 0.001 to about 20 wt %, including about 0.01 to about 10 wt %, and including about 0.05 to about 5 wt %. Of course, for any composition to be administered to an animal or human, and for any particular method of administration, it is preferred to determine therefore:

toxicity, such as by determining the lethal dose (LD) and LD50 in a suitable animal model e.g., rodent such as mouse; and, the dosage of the composition(s), concentration of components therein and timing of administering the composition(s), which elicit a suitable response.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, isotonic solution, ringer's solution, xeno-free medium, serum-free medium, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells. Sterile injectable solutions can be prepared by incorporating the cells utilized in practicing the present invention in the required amount of the appropriate solvent with various amounts of the other ingredients, as desired.

In one embodiment, the cells can be administered initially, and thereafter maintained by further administration of the cells. For instance, the cells can be administered by one method of injection, and thereafter further administered by a different or the same type of method. For example, cells can be administered by surgical injection to bring muscle function to a suitable level. The patient's levels can then be maintained, for example, by intravenous injection, although other forms of administration, dependent upon the patient's condition, can be used.

It is noted that human subjects are treated generally longer than the canines or other experimental animals, such that treatment has a length proportional to the length of the disease process and effectiveness. The doses may be single doses or multiple doses over a period of several days. Thus, one of skill in the art can scale up from animal experiments, e.g., rats, mice, canines and the like, to humans, by techniques from this disclosure and documents cited herein and the knowledge in the art, without undue experimentation. The treatment generally has a length proportional to the length of the disease process and drug effectiveness and the subject being treated.

Examples of compositions comprising the cells of the invention include liquid preparations for administration, including suspensions; and, preparations for direct or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be frozen. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected and the desired viscosity. Viscous compositions are normally prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of the cells as described in the present invention.

Compositions can be administered in dosages and by techniques available to those skilled in the medical and veterinary arts taking into consideration such factors as the age, sex, weight, and condition of the particular patient, and the composition form used for administration (e.g., solid vs. liquid). Suitable regimes for initial administration and further doses or for sequential administrations also are variable, may include an initial administration followed by subsequent administrations.

The cells described herein can also be administered in combination with other therapeutic agents or other biologically active agents. Accordingly, in one embodiment the invention also provides a composition comprising a preparation cells as described herein, at least one other therapeutic agent or biologically active agent, and a pharmaceutically acceptable diluent or carrier. The invention also provides a kit comprising a preparation of cells as described herein, or a pharmaceutically acceptable salt thereof, at least one other therapeutic agent or biologically active agent, packaging material, and instructions for administering the preparation of cells and the other therapeutic/biologically active agent or agents to an animal to treat a muscle disorder.

Certain Definitions

The terms "protein," "peptide" and "polypeptide" are used interchangeably herein.

The invention encompasses isolated or substantially purified cell compositions. In the context of the present invention, "isolated" or "purified" cell is a cell that exists apart from its native environment and is therefore not a product of nature. An "isolated" cell or a preparation of cells may exist in a purified form or may exist in a non-native environment such as, for example, a single cell suspension, or within a cell culturing (e.g., in vitro or ex vivo) container. For example, an "isolated" or "purified" preparation of cells, is substantially free of other cells such as myocytes, myoblasts, satellite cells, lymphocytes, endothelial cells or blood cells.

A preparation of cells that is substantially free of other cell types has less than about 20%, 10%, 5%, (by cell count) of contaminating cell types.

By "fragment" or "portion" is meant a full length or less than full length of the amino acid sequence of, a polypeptide or protein.

The term "agent" means an agent with affinity for a target protein so that the agent can bind the target protein. The term "anti-surface marker agent" means an agent has an affinity for the cell surface marker or binds the cell surface marker (e.g., a Cluster of Differentiation (CD) molecule) under appropriate conditions. The agent can have an optional tag as described herein.

"Culturing" or "culturing conditions" refer to cell culturing practice that maintain, expand and/or differentiate cells, for example, culturing cells in nutrient/growth factor supplemented cell growth medium in a cell culture container placed in a cell incubator (e.g., at 37 Celsius degree). Under culturing conditions, cells biochemical activities may approach that of a physiological level. In contrast, processing cells, digesting cells, centrifuging cells, washing cells, staining cells with an anti-surface marker agent is typically conducted under non-culturing conditions, such as contacting cells with a buffer (e.g., blocking buffer, washing buffer or staining buffer) and/or at low temperatures (e.g., 4 Celsius degree) that the cells biochemical activities are slowed and nutrients/growth factors level are reduced or lacking compared to culturing conditions.

The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" or "effective amount" means an amount of a preparation of cells of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein, a "subject" or an "animal" is, e.g., a mammal, e.g., a human, monkey, dog, cat, horse, cow, pig, goat, rabbit, guinea pig, hamster, rat, or mouse.

The invention will now be illustrated by the following non-limiting Examples.

Example 1. Isolation of Human Fibroadipogenic Progenitors with CD73

Skeletal muscle relies on coordination between myogenic and non-myogenic interstitial cells for homeostasis and for regeneration and response to injury. Fibroadipogenic progenitors (FAPs) have recently been recognized as key modulators of signaling to promote myogenesis following injury. FAPs are also responsible for the fibrosis and fatty replacement of muscle tissue seen in many diseased states. While extensive use of surface markers to purify FAPs has been undertaken in the mouse system, in particular PDGFRA, markers for human FAPs are less well understood. Here it was shown in this Example that CD73 can be used as a single positive marker to purify FAPs from the lineage-negative (CD45-neg, CD31-neg) of skeletal muscle mononuclear cells. Although CD73 was previously found to be expressed in cultured myogenic cells, we show that this marker is acquired upon in vitro culture and that the CD73+ fraction of human skeletal muscle has no myogenic activity. We show that Lin-neg CD73+ cells from human muscle undergo fat differentiation as well as fibrogenesis when exposed to appropriate activating signals in vitro. This simple single positive marker approach effectively enables isolation of human FAPs from fresh human skeletal muscle biopsies.

Skeletal muscle contains numerous non-myogenic supportive cell types which interact with each other and with myogenic cells to maintain muscle function and enable regenerative homeostasis. Using mouse genetic models and cell surface markers, the role of cells with fat and fibroblastic differentiation potential in coordinating the regenerative response of satellite cells to injury has become appreciated in the mouse system (Joe et al., *Nat Cell Biol* 12(2), 153-163, 2010; Murphy et al., *Development,* 138(17):3625-37, 2011; Uezumi et al., *Nat Cell Biol* 12(2), 143-152, 2010; Wosczyna et al., *Cell Rep,* 14; 27(7):2029-2035, 2019). These cells are commonly referred to as FAPs (fibroadipogenic progenitors), for their ability to differentiate into fat or matrix-secretory fibroblasts, in vitro and in vivo (Joe et al., *Nat Cell Biol* 12(2), 153-163, 2010). In the murine system, FAPs have been prospectively isolated using a combination of lineage negative (CD45, CD31, and Itga7) markers together with the positive markers PDGFRA (Uezumi et al., *Nat Cell Biol* 12(2), 143-152, 2010) or CD34 and Sca1 (Joe et al., *Nat Cell Biol* 12(2), 153-163, 2010). After severe injury, such as is generated by myotoxin injection, FAP numbers increase, but return to normal within 5 days (Joe et al., *Nat Cell Biol* 12(2), 153-163, 2010).

The importance of this cell population in muscle regeneration and injury response has been a topic of intense study in the past decade. However, there are still many unknown questions about FAP biology. One important challenge is the isolation and identification of FAPs in human skeletal muscle. Cell surface markers like PDGFRA and CD201 (Uezumi et al., *Stem Cell Reports.* 7(2):263-78, 2016) have been proposed to be used for FAP identification, but no other candidates have been identified. The best characterized mesenchymal lineage progenitor cells are mesenchymal stem cells (MSC) which are found in a variety of tissues and are known for their plasticity and immunomodulatory properties. In several contexts, MSCs have been found to express CD73 (Breitbach et al., *Cell Stem Cell,* 22(2):262-276, 2018; Dominici et al., *Cytotherapy.* 8(4):315-7, 2006). Recent studies have suggested a role for CD73 in regulating stemness of bone marrow MSCs as well as of cancer cells (Lupia et al., *Stem Cell Reports,* 10(4):1412-1425. 2018; Tan et al., *Stem Cells Int,* 8717694, 2019), suggesting that CD73 could be an identifying marker in other stem and progenitor cells. Here we investigate whether CD73 can be used as a marker to identify and sort out FAPs from freshly isolated human muscle.

Results
CD73 Excludes Human Cells with Myogenic Activity but Marks Cells with Adipogenic and Fibrogenic Activity.

Figure 1B:
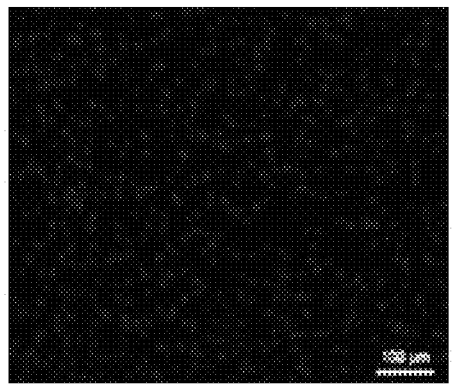
Figure 1B:
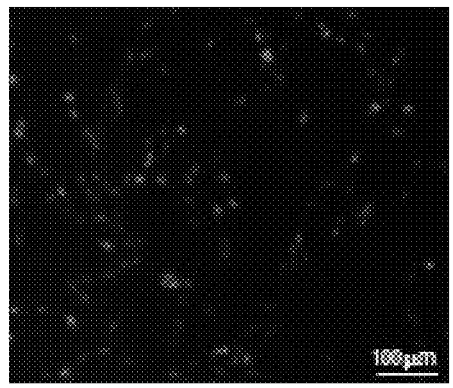
Figure 1B:
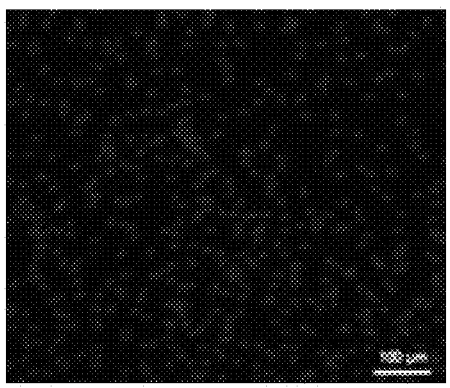
Figure 1B:
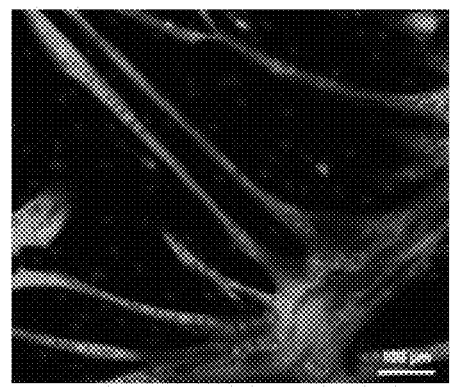
Figure 1C:
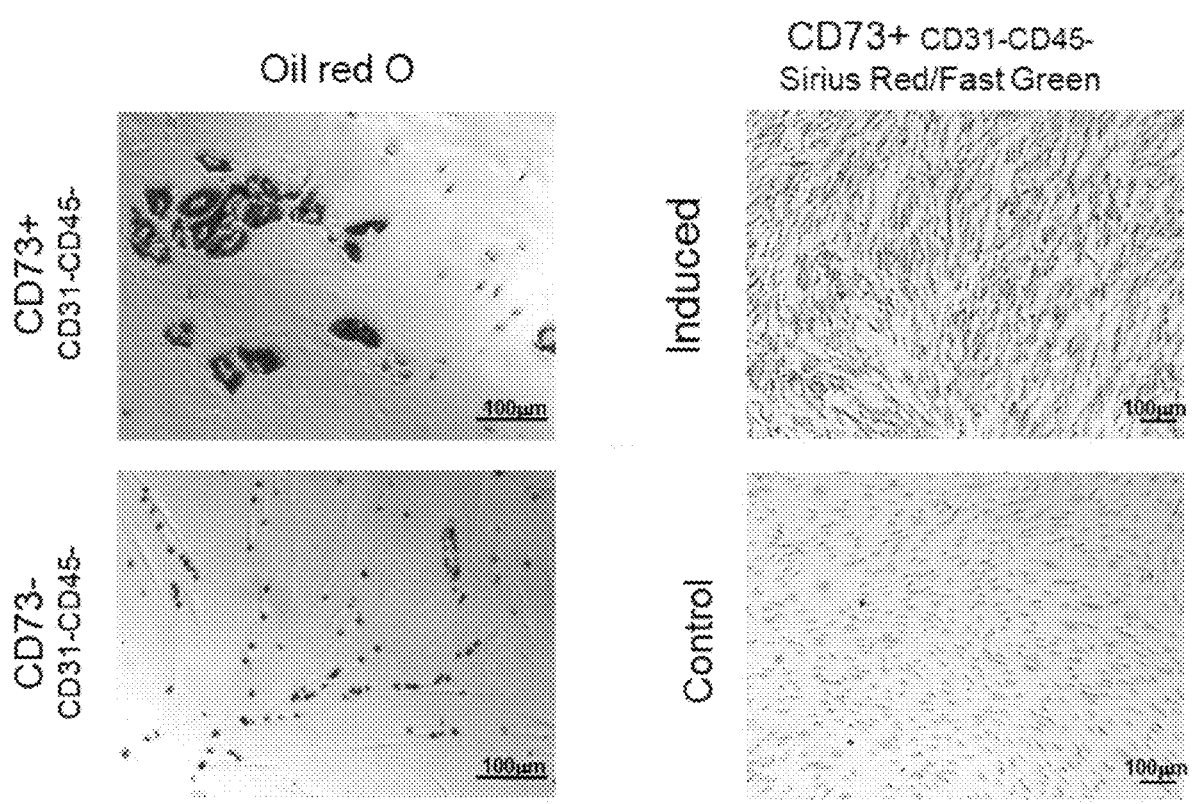

To examine the presence of cells expressing CD73 within human skeletal muscle, and to determine their phenotypic potential, normal human biopsy samples were obtained and stained with CD73, together with the endothelial and hematopoietic markers CD31 and CD45. Out of the eight samples examined, the average fraction of CD73+ cells in the lineage negative (CD45−CD31−) population was approximately 5% (FIG. 1A and Table 1). This population of cells was sorted out using FACS and cultured on gelatin coated dishes in 5% oxygen. After expansion, cells were tested for differentiation potential by replating under conditions promoting myogenic, adipogenic, or fibrogenic differentiation. Allowing cells to reach confluence and then exposing to myogenic differentiation medium revealed that CD73+ cells do not differentiate into muscle in vitro, evident by the lack myosin heavy chain (MHC) expressing myotubes. In comparison, the CD73− fraction robustly formed myotubes (FIG. 1B). Together, these data suggest that CD73 marks a population of cells in the muscle that lacks myogenic differentiation potential. To further establish the identity of this population, CD73+ cells were plated under adipogenic and fibrogenic differentiation conditions. After seven days in their respective differentiation media, the cells were stained for lipid droplets using Oil Red O or for collagen deposition using Sirius Red/Fast Green. While the CD73− lineage-population formed neither adipocytes nor cells depositing high levels of collagen, the CD73+ population readily made adipocytes or cells secreting collagen, under pro-adipogenic or pro-fibrotic conditions (FIG. 1C).

TABLE 1

Biopsy sample description

| Sample | % CD73 + CD31-CD45- | Sex | Age | Muscle |
| --- | --- | --- | --- | --- |
| MH120916 | 6.42 | M | 53 | V. lateralis |
| MH072317 | 3.65 | M | 40 | V. lateralis |
| MH180910 | 2.23 | M | 64 | V. lateralis |
| MH190626 | 5.72 | M | 17 | V. lateralis |

Transplanted CD73+ Cells Engraft in Immune-Deficient Mice, but do not Make Muscle.

Figure 2:
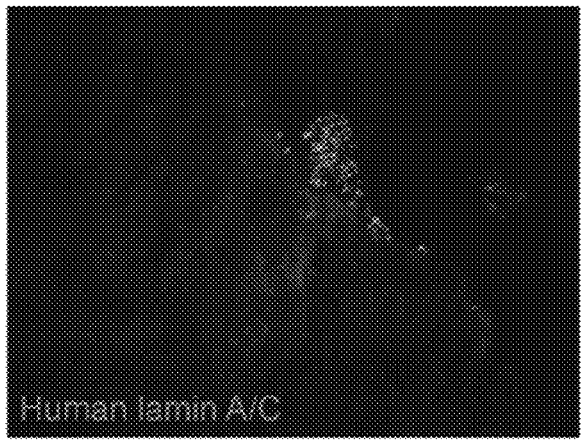
FIG. 2. CD73+ cells do not differentiate into muscle in vivo. CD73+ and CD73− cells were transplanted into NSG-mdx4$^{Cv}$ mice, which lack dystrophin. Dystrophin (red) staining of muscle cross sections indicates myogenic contribution of injected cells, revealing myogenic differentiation of CD73− cells, but an absence of myogenic contribution from CD73+ cells. Human lamin A/C (green) indicates engraftment of primary cells.
Figure 2:
Figure 2:
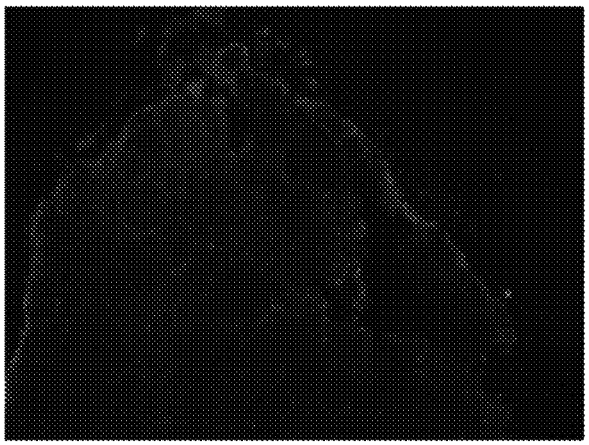
Figure 2:
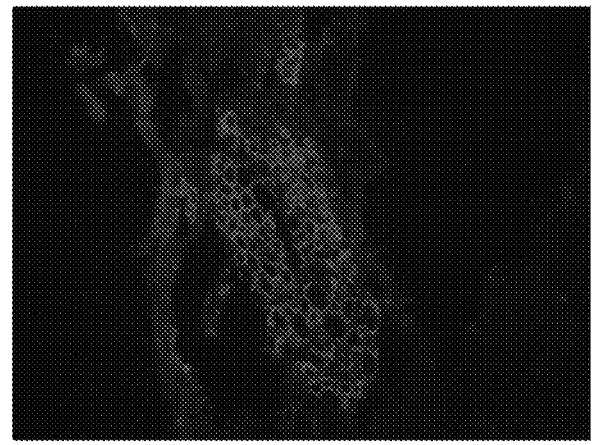

To rigorously confirm the lack of myogenic activity of CD73+ cells, we transplanted freshly isolated CD73+ lineage− cells into pre-injured, irradiated, tibialis anterior muscles of NSG-mdx$^{4Cv}$ mice (Arpke et al., Stem Cells. 31(8):1611-20, 2013). These animals lack dystrophin, thus donor-derived myofibers can be readily identified by dystrophin staining of muscle sections. As a positive control, the CD73− population was transplanted into the contralateral leg. Two months post-transplantation, whereas the CD73− population engrafted and formed dystrophin+ muscle, the CD73+ population lacked any in vivo myogenic ability (FIG. 2). Human-specific lamin A/C staining revealed human mononuclear cells derived from the CD73+ cells were nevertheless present within the transplanted muscle, indicating engraftment of primary cells. These data suggest that although these cells are capable of engraftment, they do not have any myogenic potential.

CD73 Expression is Induced Upon In Vitro Culture of Primary Myogenic Cells.

Figures 3A, 3B, 3C:
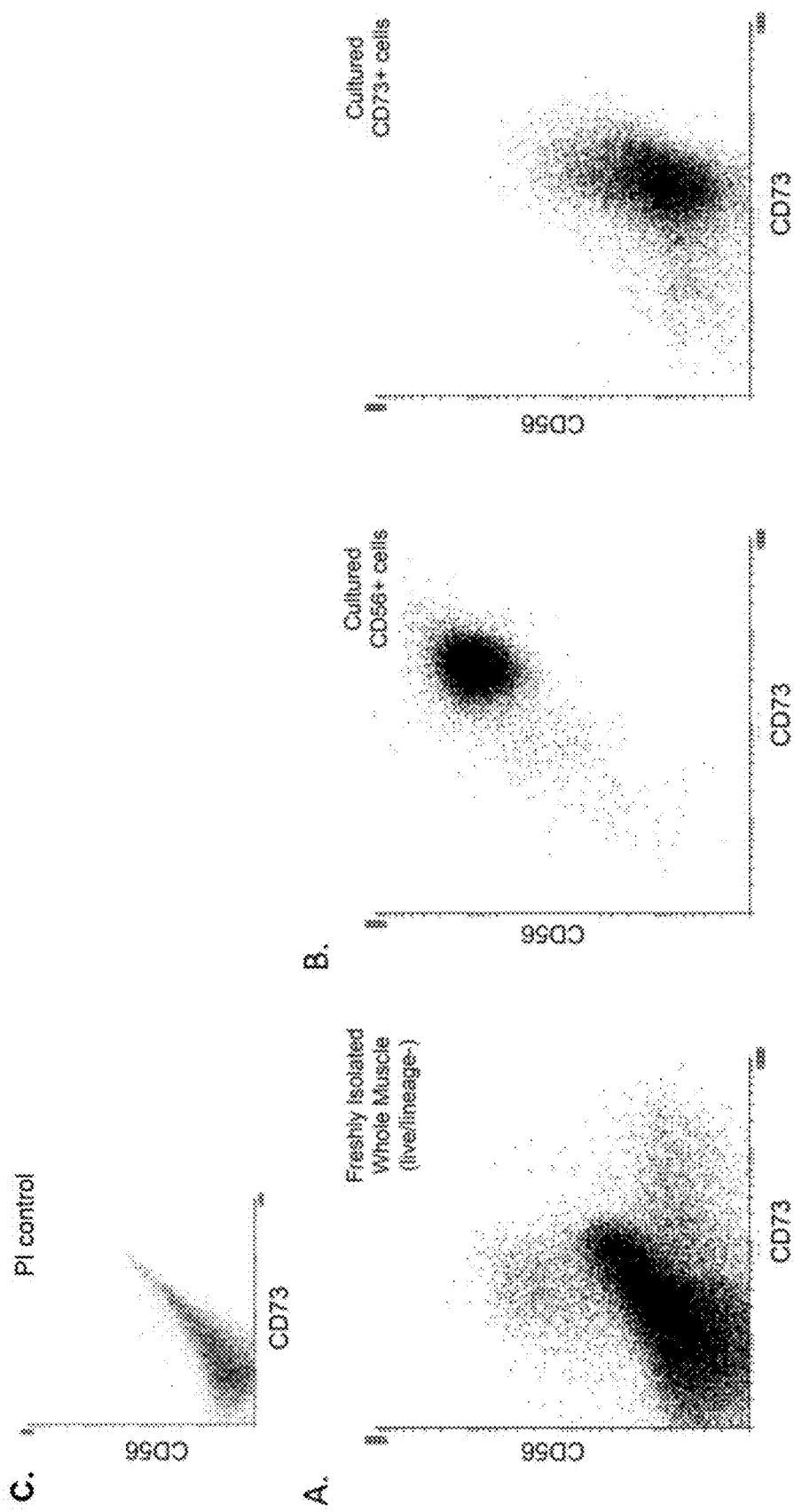
FIGS. 3A-3C. CD73 expression comes on after culture.

Previous work evaluated cell surface markers on cultured cells derived from human skeletal muscle, screening 332 markers. In this study, it was found that CD73 was expressed by both cultured myogenic progenitors (CD56+) and cultured FAPs (PDGFRA) (Uezumi et al., Stem Cell Reports. 7(2):263-78, 2016). As this result seemed contradictory to our observations, we examined this question in more detail, comparing freshly purified myogenic progenitors to their in vitro cultured derivatives. Combining CD73 and CD56 antibodies, together with the lineage negative cocktail (CD45− CD31−) and found that in fresh human muscle biopsies, distinct CD73+ and CD56+ populations exist, without overlap (FIG. 3A). The CD56+ and CD73+ populations were then sorted by FACS, cultured ex vivo for two passages, and reevaluated by FACS. This revealed that while the CD73+ population stably retained its CD73+CD56− expression profile, the CD56+ population had now became double-positive for both CD56 and CD73, demonstrating that CD73 comes on with culture in myogenic cells (FIG. 3B).

Discussion

In this study, it was demonstrated that CD73 marks the FAP population in freshly isolated human skeletal muscle. Our data show that freshly isolated CD73+ cells are non-myogenic cells which are capable of both adipogenic differentiation and fibrogenesis in vitro. Furthermore, when transplanted into immunodeficient dystrophin-deficient mice, they engraft but do not form muscle fibers. In aggregate, these data suggest that CD73 marks the resident FAP population of human skeletal muscle. Interestingly, a previous study identified a CD73+CD105+ mesenchymal population that was likely responsible for heterotopic muscle ossification (Downey et al., Bone. 71:164-70, 2015). The CD73+ population that can undergo both adipogenesis and fibrogenesis in vitro identified here may include this double positive population with bone-forming potential, and supports the notion that FAPs are responsible for heterotopic ossification.

An earlier study examining cell surface markers of mesenchymal and myogenic populations in human skeletal muscle looked at ex vivo expanded CD56+ (myogenic) and PDGFRA+ (mesenchymal) populations (Uezumi et al., Stem Cell Reports, 7(2):263-78, 2016). They examined CD73 expression in response to the findings by Downey et al., Bone. 71:164-70, 2015, but found that both the in vitro cultured CD56 and PDGFRA populations were CD73+ (Uezumi et al., Stem Cell Reports. 7(2):263-78, 2016), thus considering that CD73 would not be useful as a positive marker for prospective isolation. Our work explains this apparent discrepancy by showing that freshly isolated myogenic cells only gain CD73 expression after ex vivo culture, highlighting the importance of considering how markers may change with in vitro culture.

In summary, CD73 is a robust marker for the identification and isolation of FAPs from fresh human skeletal muscle.

Materials and Methods

Biopsy Tissue Processing and Flow Cytometry

Human muscle tissue samples from the vastus lateralis muscle were obtained after donor consent either by needle biopsy or from surgical waste tissue after diagnostic surgical biopsies. Muscle tissue was mechanically separated and digested with 0.2% collagenase II for 30 minutes at 37 C. Mononuclear cells were washed and resuspended in maintenance media (F10 (HyClone) supplemented with 20%

FBS, 2-mercaptoethanol, $10^{-9}$M dexamethasone (Sigma), 10 ng/mL bFGF (Peprotech)), Glutamax (GIBCO) and Penicillin/Streptomycin (P/S, GIBCO). Human tissue procurement was conducted under a protocol approved by the University of Minnesota Institutional Review Board. Freshly isolated cells were analyzed and sorted on the BD Aria II flow cytometer using the following antibodies: CD73 (APC, Clone AD2, 17-0739-42), CD56 (APC, Clone CMSSB, 17-0567-42), CD45 (PE-Cy7 Clone H130, BDB557748), CD31 (PE-Cy7 Clone WM-595, BDB563651) (see, Goloviznina, et al., *Heliyon*, 6(7): e04503, 2020, which is incorporated by reference herein for all purposes).

In Vitro Differentiation

To examine adipogenic and fibrogenic differentiation potential, CD73+ cells were plated in expansion medium (F10 (HyClone) supplemented with 20% FBS, 2-mercaptoethanol, 10-9 M dexamethasone (Sigma), 10 ng/mL bFGF (Peprotech), Glutamax (GIBCO) and Penicillin/Streptomycin (P/S, GIBCO)) until confluency. Then medium was changed to adipogenic medium (DMEM high glucose supplemented with 10% FBS, penicillin-streptomycin, 0.2 mM indomethacin, 0.5 mM 3-isobutyl-1-methylxanthine, 10 µg/ml recombinant human insulin and 1 µM dexamethasone) or fibrogenic medium (10 ng/ml TGFβ) for 5-7 days. At the termination of differentiation cells were stained with Oil Red 0 (Sigma, #00625-25G) and Sirius Red/Fast Green (Chondrex, #9062) to examine adipogenesis and fibrogenesis respectively. Immunostaining was performed on 4% paraformaldehyde fixed cells, treated with 0.2% Triton X-100, blocked with 3% BSA. Primary and secondary fluorochrome conjugated antibodies were diluted in 3% BSA and incubated overnight at 4° C. or for 1 hour at room temperature. Antibodies used: mouse anti-MHC (MF20, 1:20, Developmental Studies Hybridoma Bank), Alexa fluor 488 Goat Anti-Mouse, 4',6-diamidino-2-phenylindole (DAPI, Invitrogen).

Transplantation Studies

Freshly isolated CD73+CD45−CD31− cells were engrafted into the tibialis anterior muscle of NSG-mdx$^{4Cv}$ mice (Arpke et al., *Stem Cells*. 31(8):1611-20, 2013). Briefly, recipients were treated with cardiotoxin then 24-hours later x-ray irradiated (1200 cGy), then 24-hours following the irradiation $4 \times 10^4$ cells were injected. Freshly isolated CD73−CD45−CD31− cells were injected in the contralateral leg as a myogenic engraftment comparison. Three weeks later the muscle was removed and cryosectioned to analyze engraftment. Sections with anti-human lamin A/C and anti-dystrophin to examine engraftment and myogenic contribution. Briefly, sections were fixed for 20 minutes with 4% PFA, permeabilized with 0.2% Triton X-100, blocked for one hour at room temperature with 3% BSA, incubated with primary antibody (mouse anti-human lamin A/C, clone 4C11; rabbit anti-dystrophin, AB15277-1) overnight at 4 C. Animal work was conducted under a protocol approved by the University of Minnesota Institutional Animal Care and Use Committee.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and "or" and similar referents in the context of describing the invention are to be construed to cover both the singular and the plural, unless otherwise indicated herein or clearly contradicted by context. Thus, for example, reference to "a subject polypeptide" includes a plurality of such polypeptides and reference to "the agent" includes reference to one or more agents and equivalents thereof known to those skilled in the art, and so forth.

The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention. Further, all publications mentioned herein are incorporated by reference in their entireties.

What is claimed is:

1. A method of producing a preparation of fibroadipogenic progenitors (FAPs), comprising:
   contacting a cell mixture comprising FAPs with an anti-CD73 agent having affinity for CD73, wherein the agent has an optional tag, and
   separating the anti-CD73 agent labeled cells from the cell mixture to produce the preparation of FAPs,
   wherein the cell mixture is not contacted with an additional positive co-staining selection agent,
   wherein the cell mixture is dissociated from a human skeletal muscle tissue sample comprising FAPs,
   wherein the cell mixture is not cultured under culturing conditions prior to contacting with the anti-CD73 agent, and
   wherein myogenic cells are excluded by contacting the cell mixture with the anti-CD73 agent and separating the anti-CD73 agent labeled cells from the cell mixture.

2. The method of claim 1, further comprising obtaining the cell mixture comprising the FAPs and/or culturing the preparation of FAPs under culturing conditions.

3. The method of claim 1, wherein the cell mixture dissociated from the tissue sample is contacted with the anti-CD73 agent within 12 hours after dissociation from the tissue sample.

4. The method of claim 1, wherein the tissue sample is a skeletal muscle biopsy sample.

5. The method of claim 1, wherein the separating comprises conducting fluorescence-activated cell sorting (FACS) and/or magnetic-activated cell sorting (MACS) to produce the preparation of FAPs.

6. The method of claim 1, wherein the anti-CD73 agent is an antibody, fragment or derivative thereof, an affibody, or an aptamer.

7. The method of claim 1, wherein the anti-CD73 agent labeled cells have reduced CD73 cell surface expression levels and/or reduced CD73 enzymatic activity levels as compared to the FAPs prior to being contacted with the anti-CD73 agent.

8. The method of claim 1, further comprising
   contacting the cell mixture with a negative selection co-staining agent(s), and
   separating negative selection co-staining agent(s) labeled cells from the cell mixture comprising the FAP cells.

9. The method of claim 8, wherein the negative selection co-staining agent(s) has affinity for marker(s) of an endothelial lineage cell, hematopoietic lineage cell, or satellite cell.

10. The method of claim 8, wherein the negative selection co-staining agent(s) has affinity for CD31, CD45, CD9, CD46, CD81, CD83, CD97, FGFR4, TGFBR3, or CXCR4.

11. The method of claim 8, wherein the separating of the negative selection co-staining agent labeled cells comprises conducting FACS and/or MACS to exclude non-FAP cells from the preparation of FAPs.

12. The method of claim 8, wherein the negative selection co-staining agents comprise an anti-CD31 agent and an anti-CD45 agent.

13. The method of claim 1, further comprising culturing the preparation of FAPs under conditions sufficient to produce a preparation of differentiated cells derived from the FAPs.

14. The method of claim 1, wherein the anti-CD73 agent is linked to a tag.

15. The method of claim 14, wherein the tag is a fluorochrome, polypeptide tag, biotin, quantum dot, or magnetic particle.

* * * * *